United States Patent [19]

Shah

[11] Patent Number: 4,835,296

[45] Date of Patent: May 30, 1989

[54] PROCESS FOR PREPARING UNSYMETRICAL HYDROCARBONTIN CHLORIDES

[75] Inventor: Harnish V. Shah, Columbia, S.C.

[73] Assignee: Cardinal Research & Development Co., Inc., Columbia, S.C.

[21] Appl. No.: 45,416

[22] Filed: May 1, 1987

[51] Int. Cl.$^4$ .............................................. C07F 7/22
[52] U.S. Cl. ..................................................... 556/97
[58] Field of Search ........................................... 556/97

[56] References Cited

U.S. PATENT DOCUMENTS

| | | | |
|---|---|---|---|
| 2,608,567 | 8/1952 | Johnson et al. | 556/97 |
| 3,036,103 | 5/1962 | Johnson | 556/97 X |
| 3,069,448 | 12/1962 | Reindl et al. | 556/97 |
| 3,297,732 | 1/1967 | Banks | 556/97 X |
| 3,389,158 | 6/1968 | Kushlefsky | 556/97 |

Primary Examiner—Paul F. Shaver

[57] ABSTRACT

A process is described for preparing high purity unsymetrical hydrocarbontin chlorides in less than one hour at temperatures below 90° C. utilizing a combination catalyst-complexing agent resulting in yields above 98%.

3 Claims, No Drawings

PROCESS FOR PREPARING UNSYMETRICAL HYDROCARBONTIN CHLORIDES

This invention relates to a process for the manufacture of unsymetrical hydrocarbon tin chlorides. More specifically, it relates to a process which yields higher purity than previously reported trihydrocarbontin chlorides.

As is known by those practicing the art, hydrocarbontin compounds are presently made by a disproportionation reaction:

Theoretically, the reactions proceed as follows:

$$R_4Sn + SnCl_4 \rightarrow R_3SnCl + RSnCl_3 \quad (1)$$

$$R_3SnCl + SnCl_4 \rightarrow R_2SnCl_2 + RsnCl_3 \quad (2)$$

$$R_2SnCl_2 + SnCl_4 \rightarrow 2RSnCl_3 \quad (3)$$

$$R_4Sn + R_2SnCl_2 \rightarrow 2R_3SnCl \quad (4)$$

$$R_3SnCl + RSnCl_3 \rightarrow R_2SnCl_2 \quad (5)$$

Although the equations balance nicely, the processes reach an equilibrium at about 95% and it has heretofore not been possible to prepare high purity unsymetrical hydrocarbontin chlorides by disproportioning.

Banks discloses in U. S. Pat. No. 3,297,732 that aluminum chloride may be used as a cross-alkylation catalyst. It is apparent that this procedure is less than satisfactory in that example one of the patent shows a 72% yield of dibutyltin dichloride of low purity. Additionally, the process requires the use of a solvent and then chilling the solvent to below −20° C. which commercially is not an acceptable process. Other examples disclosed in this patent further indicate the difficulty and lack of success in obtaining high purity unsymetrical hydrocarbontin chlorides.

The difficulty of preparing specific unsymetrical compounds is most apparent in the butyltin chlorides and octyltin chlorides.

The butyltins have very close boiling points; i.e., Tributyltin Chloride boils at approximately 142° C., 10 mm Hg, whereas Tetrabutyltin at the same pressure is 145° C., and Dibutyltin Dichloride is 135° C. Separation by recrystallization or solvent extraction is also not practical due to low recovery.

The octyltins are high boiling and separation by thermal or extractive processes yield highly colored fractions.

It has now been discovered that unsymetric hydrocarbontin compounds especially trihydrocarbontin chlorides can be prepared in yields close to theoretical, in high purity, and at low temperatures. This is accomplished by using a disequilibrium catalyst comprising a trivalent metal chloride and an ether complex preferably containing eight but more than 2 carbon atoms and less than 14 carbon atoms.

Typically, the catalyst of choice is aluminum trichloride and dibutyl ether.

Other metal or metalloid trivalent chlorides may be used such as $FeCl_3$, $BiCl_3$, $PCl_3$, $AsCl_3$, $SbCl_3$, $BCl_3$.

Typical ethers such as diisopropyl, di-n-propyl, propyl butyl, diphenyl, methyl tertiary butyl or tetrahydrofuran may be used with the trivalent metallic chloride.

The embodiment of this invention is shown in the following examples:

EXAMPLE I

This example illustrates the practice of the invention according to the reaction:

$$(C_4H_9)_4Sn + (C_4H_9)_2SnCl_2 \rightarrow 2(C_4H_9)_3SnCl$$

The apparatus consisted of a one liter three-neck flask with a heating mantle.

The flask was fitted with a reflux condenser, a thermometer 0°–150° C., and a propeller type agitator.

The flask was charged with 347.2 g (one mol) of tetrabutyltin; 303.8 g (one mol) dibutyltin dichloride; 39.1 g (⅓ mol) dibutyl ether; and 40.0 g (⅓ mol) of aluminum chloride.

The mixture was heated with agitation to 75°–80° C. for 45 minutes and then cooled to 25° C.

The aluminum chloride was extracted with 93 g of 0.5% hydrochloric acid solution. The residual water and dibutyl ether were removed under vacuum (20 mm hg pressure) at 110° C.

G. C. analysis indicated the composition contained 99.25% tributyltin chloride and 0.75% dibutyltin dichloride with an overall gravimetric yield of 99%.

EXAMPLE II

The procedure of example one was repeated. The G. C. analysis indicated 97.68% tributyltin chloride; 1.6% dibutyltin dichloride and 0.8% tetrabutyltin. The overall gravimetric yield was above 97%.

EXAMPLE III

This example illustrates the practice of the invention according to the reaction:

$$3(C_4H_9)_4Sn + SnCl_4 \rightarrow 4(C_4H_9)_3SnCl$$

The apparatus described in Example One was used.

1041.5 g (3 mol) of tetrabutyltin and 39.1 g (0.3 mol) of dibutyl ether were charged into the flask. 260.5 g (1 mol) of stannic chloride was added. The temperature rose to 50° C. After ten minutes, 40 g (0.3 mol) of aluminum chloride was added and the temperature rose to 55° C.

The mixture was then heated to 75°–80° C. for 45 minutes, cooled and the $AlCl_3$ extracted with 93 g of 0.5% HCl solution.

The dibutyl ether was removed under 20 mm Hg reduced pressure.

Analysis by G. C. showed 98.5% tributyltin chloride, 0.86% tetrabutyltin and 0.65% dibutyltin dichloride with an overall yield of 98.7%.

EXAMPLE IV

The procedure of example one was followed using $AlCl_3$ and without any dibutyl ether.

The conversion to tributyltin chloride was less than 72%.

EXAMPLE V

The procedure of example three was followed using $AlCl_3$ and without any dibutyl ether. The conversion to tributyltin chloride was 76%. The temperature was then raised to 200° C. or 110° C. higher than the claim of this invention. The conversion to tributyltin chloride was 92% after 2½ hours.

I claim:

1. The process for preparing tributyltin chloride which comprises reacting tetrabutyltin with dibutyltin dichloride or with stannic chloride in the presence of an aluminum trichloride-dibutylether disequilibrium catalyst.

2. The process of claim one wherein the reaction temperature is between 25° C. and 100° C.

3. The process of claim one wherein the catalyst is between one and ten percent by weight of the hydrocarbontin used.

* * * * *